United States Patent [19]
Kusy et al.

[11] Patent Number: 5,869,178
[45] Date of Patent: Feb. 9, 1999

[54] PULTRUDED FIBER-REINFORCED PLASTIC AND RELATED APPARATUS AND METHOD

[75] Inventors: Robert P. Kusy; Kenneth C. Kennedy, II, both of Chapel Hill, N.C.

[73] Assignee: The University of North Carolina at Chapel Hill, Chapel Hill, N.C.

[21] Appl. No.: 295,540

[22] Filed: Aug. 25, 1994

[51] Int. Cl.$^6$ ...................................................... B32B 1/00
[52] U.S. Cl. ........................... 428/335; 428/330; 428/331; 428/332; 428/333; 428/334; 428/337; 522/908; 433/20
[58] Field of Search ..................................... 428/334, 337, 428/335, 330, 331, 332, 333; 522/908; 433/20

[56] References Cited

U.S. PATENT DOCUMENTS

| | | |
|---|---|---|
| 4,462,946 | 7/1984 | Goldsworthy .............................. 264/23 |
| 4,717,341 | 1/1988 | Goldberg et al. ........................... 433/9 |
| 4,894,012 | 1/1990 | Goldberg et al. ......................... 433/215 |

OTHER PUBLICATIONS

Advanced Polymer Composites, Bor Z. Jang pp. 64 & 65.
Jancar et al., "Thermoplastic Fibre–Reinforced Composites for Dentistry", vol. 4, *Journal of Materials Science: Materials in Medicine*, pp. 562–568 (Dec., 1993).
Patel et al., "The Effect of Thermoforming on the Properties of Fiber–Reinforced Composite Wires", vol. 3, *Journal of Applied Biomaterials*, pp. 177–182 (1992).
Goldberg et al., "The Use of Continuous Fiber Reinforcement in Dentistry", vol. 8, *Dental Materials*, pp. 197–202 (May, 1992).

*Primary Examiner*—Richard Weisberger
*Attorney, Agent, or Firm*—Richard E. Jenkins, P.A.

[57] ABSTRACT

Disclosed are profiles of fiber-reinforced polymeric plastic and a pultrusion apparatus and method for the manufacture thereof. The apparatus is preferably vertically disposed. As one or more fibers is fed into the apparatus, each fiber is spread and wetted with monomer resin in a bundle spreader, formed in a die, and then subjected in a curing chamber to a source of radiation which initiates polymerization of the monomer, resulting in a fiber-reinforced polymeric plastic exiting from the pultrusion apparatus. Suitably, the radiation is ultraviolet, the monomer resin is methacrylate resin, and the fiber is quartz. The resultant profile is long and thin like a structural steel wire, but typically will have only ¼ the weight thereof while having a strength comparable thereto. Thus, the profile is useful as an orthodontic wire as a replacement instead of structural steel wires used as orthodontic wires. Several profiles can also be aggregated and the aggregate used to make, for instance, artificial limbs or other structural products.

15 Claims, 8 Drawing Sheets

35%

39%

47%

54%

62%

70%

PULTRUDED FIBER-REINFORCED PLASTIC AND RELATED APPARATUS AND METHOD

TECHNICAL FIELD

The present invention relates, in general, to profiles of pultruded fiber-reinforced plastic, i.e. polymeric plastic that via pultrusion has had its mechanical strength properties reinforced with fiber, and a pultrusion apparatus for manufacturing such pultruded composites of plastic and fiber. More particularly, the present invention relates to novel pultruded fiber-reinforced plastic that is strong (has a tensile strength comparable to that of a similarly sized structural steel wire), yet is light weight (typically, has a weight ¼ that of a similarly sized structural steel wire) and that has a cross-section that is extremely thin. Also, the present invention relates to a novel apparatus for manufacturing such strong and thin pultruded fiber-reinforced plastic. Especially, the novel pultruded fiber-reinforced plastic is useful as an orthodontic arch wire or face bow and thus can replace the steel wire presently used therefor.

RELATED ART

In current pultrusion processes, typical commercially available fibers used for manufacturing pultruded composites have been fibers such as aramid fiber (a type of nylon sold under the trade name KEVLAR™ by DuPont Corporation of Wilmington, Del.), glass fiber (S-2 and E), quartz fiber, graphite fiber, and others. The fiber is commercially available as a yarn or roving, i.e., a twisted "bundle" or untwisted "bundle", respectively, of individual filaments, on a spool. Such fibers have been processed with a horizontally disposed pultrusion apparatus.

More specifically, fibers are horizontally pulled through the pultrusion apparatus, wherein the fibers are coated (wetted) with a monomer resin (containing a polymerization initiator). Next, the monomer resin is cured with heat (and often also pressure), as a result of which the monomer resin polymerizes thereby producing pultruded fiber-reinforced plastic of higher strength than un-reinforced polymer. Hence, the plastic and fiber are adhered or bonded together in a strong product.

During curing, the wetted fiber is shaped into a profile. In other words, the wetted fiber is formed into a desired cross-sectional morphology, which will often range from generally circular to generally rectangular. Depending on the intended end use of the pultruded product, it may be further shaped into a different morphology.

Further shaping of a profile of pultruded product is colloquially referred to as "beta-staging". Beta-staging is usually accomplished with heat, particularly if the plastic is a thermoplastic. However, it can be achieved by first only partially curing the resin when making the profile of pultruded fiber-reinforced plastic, and then re-shaping followed by beta-staging to finish the curing after re-shaping so that finishing will set the modified shape of the profile.

Of course, shaping the profile of wetted fiber during curing or further shaping during beta-staging after manufacture of the pultruded product can include making the profile straight or making it bent or curved. In other words, the profile can be shaped longitudinally as well as in the cross-sectional directions.

The prior art profiles (pultruded fiber-reinforced plastic) can range in size from being relatively thick in cross-section, with a cross-sectional dimension of approximately 3 feet (91.4 cm), to being relatively small in cross-section, with a generally rectangular crosssection of approximately 0.02 inch×0.50 inch (0.05 cm×1.27 cm). Such prior pultruded products have many uses, one being the reinforcement of concrete. Other uses are shelving struts, ladder struts, and window frames. In particular, pultruded glass fiber-reinforced plastic is very representative of the prior art, and commercially competes with aluminum extrusions.

Clearly, it would be desirable to have improved pultruded fiber-reinforced plastic, and an apparatus for the production thereof, wherein the improved pultruded composite of plastic and fiber were very thin yet had a strength and/or stiffness comparable to and/or better than that of prior art pultruded fiber-reinforced plastic. Such would especially be expedient when the use of the pultruded composite would be facilitated if the pultruded composite were very thin.

With the presently available technology for the manufacture of pultruded fiber-reinforced plastic (a typical pultruded composite being about 50% by volume polymer and 50% by volume fiber), the resultant profile is typically thick in order to be strong. Using the present technology and pultrusion apparatuses, a very thin profile of pultruded fiber-reinforced plastic (a typical product being about 50% by volume polymer and 50% by volume fiber) having a generally circular cross-section ranging from about 0.012 to about 0.025 inch (from about 0.030 to about 0.063 cm) in diameter, has not been manufactured with such good mechanical properties as the profiles of the instant invention.

The following journal articles are of interest with regard to pultruded profiles.

Thin, pultruded, fiber-reinforced plastic, specifically continuous S-2 glass fiber-reinforced polyethylene-terephthalate glycol of cross-sectional dimensions of 0.483 mm×0.635 mm, has been reported by Jancar, Dibenedetto, Hadziinikolau, Goldberg, and Dianselmo, in "Measurement of the Elastic Modulus of Fiber-Reinforced Composites Used as Orthodontic Wires", Vol. 5, *Journal of Materials Science: Materials in Medicine*, pp. 214–218 (1994).

Fiber-reinforced plastics, approximately 0.5×2×40 mm long, have been reported by Goldberg, Burstone, Hadjinikolaou, and Jancar, in "Screening of Matrices and Fibers for Reinforced Thermoplastics Intended for Dental Applications", Vol. 28, *Journal of Biomedical Materials Research*, pp. 167–173 (1994).

The possible clinical application of fiber-reinforced composites for treatment of misaligned teeth has been suggested by Jancar and Dibenedetto, in "Fiber-Reinforced Thermoplastic Composites for Dentistry", Vol. 4, *Journal of Materials Science: Materials in Medicine*, pp. 555–561 (1993).

The effect on deterioration of the matrix-fiber interface caused by moisture on the flexural properties of E-glass fiber-reinforced polycarbonate, E-glass fibre-reinforced poly (ethylene terephthalate glycol), and E-glass fiber-reinforced nylon has been reported by Jancar, Dibenedetto, and Goldberg, in "Thermoplastic Fibre-Reinforced Composites for Dentistry", Vol. 4, *Journal of Materials Science: Materials in Medicine*, pp. 562–568 (1993).

Fiber-reinforced composites using S-2 glass or aramid as the fiber are reported by Patel, Goldberg, and Burstone, in "The Effect of Thermoforming on the Properties of Fiber-Reinforced Composite Wires", Vol. 3, *Journal of Applied Biomaterials*, pp. 177–182 (1992).

Fiber-reinforce composite formulations, such as S-2 glass fiber-reinforced poly(ethylene terephthalate glycol), are reported by Goldberg and Burstone, in "The Use of Continuous Fiber Reinforcement in Dentistry", Vol. 8, *Dental Materials*, pp. 197–202 (May, 1992).

SUMMARY OF THE INVENTION

Accordingly, the present invention provides a profile comprising a thin pultruded fiber-reinforced plastic of about 9% to about 91% by volume polymeric plastic and about 91% to about 9% by volume fiber. More preferably, the profile of thin pultruded fiber-reinforced plastic comprises about 20% to about 80% by volume polymeric plastic and about 80% to about 20% by volume fiber. Most preferably, the profile of thin pultruded fiber-reinforced plastic comprises about 30% to about 70% by volume polymeric plastic and about 70% to about 30% by volume fiber.

It is noted that the term "fiber", specifically as used herein with respect to the present invention, is intended to mean a bundle of individual filaments and also to include in the meaning one filament. Thus, in addition to the resultant pultruded product of the instant invention being a composite of plastic and fiber, wherein each fiber is a "bundle" of filaments as per the profiles that were made, conceivably, the resultant pultruded product of the instant invention could be a composite of polymeric plastic and fiber, wherein each fiber is one filament. Also, the fibers in the pultruded product could be a combination of fiber bundles and fiber filaments.

Additionally, the present invention provides a pultrusion apparatus for forming a profile of thin pultruded fiber-reinforced plastic containing from about 9% to about 91% by volume of polymeric plastic and from about 91% to about 9% by volume fiber. The pultrusion apparatus comprises a rack holding at least one spool of fiber so that the fiber is pulled off the spool and also comprises a bundle spreader through which the fiber is pulled after leaving the spool.

The bundle spreader comprises a spreader entrance and a spreader exit, together with an alternating sequence of disks and cams beginning with and ending with a disk, wherein each disk is provided with an aperture therethrough. Additionally, the bundle spreader comprises monomer resin contained therein, such that the fiber while in the bundle spreader is spread by the disks and cams and simultaneously wetted with the monomer resin.

The pultrusion apparatus further comprises a forming die through which the wetted fiber is pulled after exiting the spreader exit of the bundle spreader, the forming die having a chamber entrance and a chamber exit. The forming die entrance is operatively associated with the spreader exit for receiving the wetted fiber to be fed into the forming die, and the forming die entrance further defines a funnel for forming the wetted fiber into a profile of predetermined morphology. The forming die has a curing chamber therein.

Also, the pultrusion apparatus comprises a radiation source operatively associated with the curing chamber to provide radiation thereto so that the wetted fiber, while being pulled through the curing chamber and formed into a profile, is subjected to radiation to cure the monomer resin of the wetted fiber and change the monomer resin into polymeric plastic.

Lastly, the pultrusion apparatus comprises a winder element to which the fiber is attached for pulling the profile of cured fiber-reinforced polymeric plastic out of the exit of the forming die (which is the same as the exit of the curing chamber) and collecting the profile thereon.

Furthermore, the present invention provides a method for forming a profile of thin pultruded fiber-reinforced plastic containing from about 9% to about 91% by volume of polymeric plastic and from about 91% to about 9% by volume fiber with a pultrusion apparatus, the pultrusion apparatus comprising a rack, a bundle spreader, a forming die with a curing chamber therein, and a winder element.

The method comprises placing at least one spool of fiber on the rack and comprises providing a bundle spreader. The bundle spreader comprises a spreader entrance and a spreader exit, and also an alternating sequence of disks and cams beginning with and ending with a disk, wherein each disk is provided with an aperture therethrough.

The method further comprises pulling the fiber off the spool and into and through the bundle spreader and providing monomer resin in the bundle spreader such that the fiber while in the bundle spreader is spread by the disks and cams and simultaneously wetted with monomer resin.

Additionally, the method comprises pulling the wetted fiber from the bundle spreader and into and through the forming die and curing chamber therein, the forming die having an entrance and an exit. The entrance is operatively associated with the spreader exit for receiving the wetted fiber to be fed into the forming die and curing chamber therein and the entrance further defines a funnel for forming the wetted fiber into a profile of predetermined morphology.

Also, the method comprises providing a radiation source operatively associated with the curing chamber to provide radiation thereto so that the wetted fiber, while being pulled through the forming die and through the curing chamber therein and formed into a profile, is subjected to radiation to cure the monomer resin of the wetted fiber and change the monomer resin into polymeric plastic. Lastly, the method comprises providing a winder element to which the fiber is attached for pulling the profile of cured fiber-reinforced polymeric plastic out of the exit of the forming die, and collecting the profile thereon.

Hence, it is an object of the present invention to provide a profile comprising thin, pultruded fiber-reinforced plastic.

It is a further object of the present invention to provide a pultrusion apparatus and pultrusion method for making such thin, pultruded fiber-reinforced plastic.

Accordingly, it is an advantage of the present invention that the profile can be very thin, yet strong and of desired stiffness, which was unobtainable with prior art profiles of pultruded fiber-reinforced plastic. In the preferred embodiment, the inventive profile has a tensile strength comparable to that of structural steel wire and thus the present profile is useful as a replacement for thin steel wire, particularly wire used in orthodontic arches and face bows since the preferred inventive profile also has a flexure modulus appropriate therefor.

Some of the objects and advantages of the invention having been stated above, other objects and advantages, will become evident as the description proceeds, when taken in connection with the examples and the accompanying drawings as best described below.

DETAILED DESCRIPTION OF THE INVENTION

Figure 1:
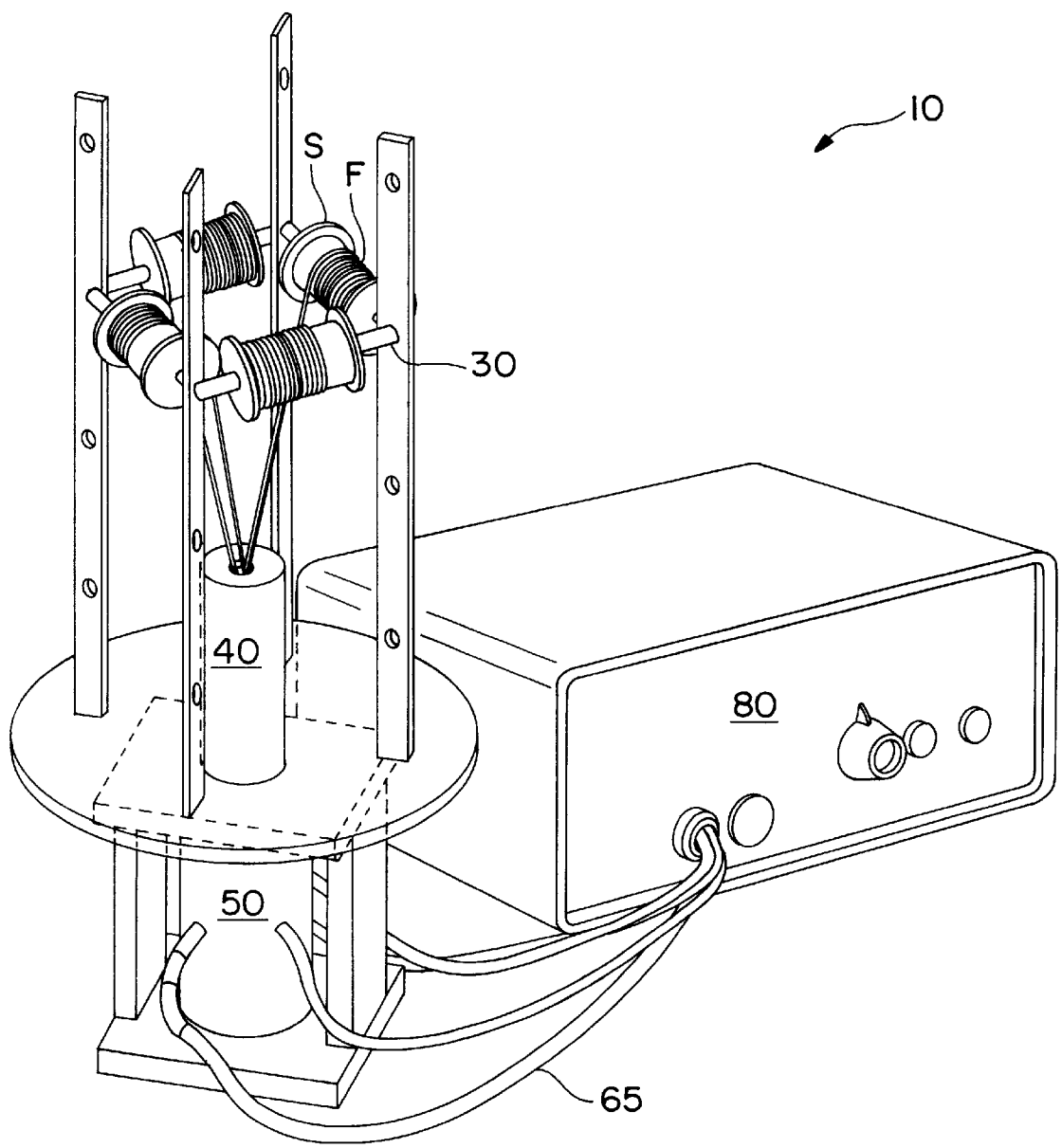
FIG. 1 is a perspective view of a vertically disposed pultrusion apparatus according to the present invention.

In the discussion below, the examples of the profiles of pultruded fiber-reinforced plastic product that were made are described in conjunction with the Figures illustrating the pultrusion apparatus. However, the following is first generally noted with regard to both the profiles and the apparatus.

When plastic has been reinforced with continuous, aligned fiber(s), usually, the pultruded product is referred to as a profile of pultruded fiber-reinforced plastic. Also, since the pultruded product is a composite of plastic and fiber, sometimes it is referred to as a fiber-reinforced composite. Thus, the terms "fiber-reinforced plastic" and "fiber-reinforced composite" are interchangeable, and herein both are intended to refer to the resultant pultruded product. In general, the pultruded product is referred to herein as a profile of pultruded fiber-reinforced plastic, which, for simplicity is abbreviated as FRP.

Various kinds of commercially available fiber, including, but not limited to, polyethylene fiber (including ultra high molecular weight polyethylene fiber), nylon fiber, polymer fiber, glass fiber (S2 and E), graphite fiber, quartz fiber, metal fiber, ceramic fiber, boron fiber, aluminum fiber, or combinations thereof, are suitable for use in the present invention. As noted above, fiber is commercially available as yarn or roving that is a bundle of individual filaments on a spool. Various companies that sell these spools of fiber are Owens Corning, Pittsburgh Plate Glass, and Allied Signal. As further discussed below, in the present invention, a rack holds one or more spools of fiber on the pultrusion apparatus.

Furthermore, various kinds of commercially available monomer resins, for forming fiber-reinforced polymeric plastic, are suitable for use in the present invention, as long as the monomer resin can be cured, i.e., polymerized, when subjected to the radiation source while the fiber wetted with the monomer is in the curing chamber of the pultrusion apparatus. Various companies that sell these monomer resins and the components thereof are Polysciences, Aldrich, and Sartomer. Typical monomer resins include, but are not limited to, acrylic monomer resin, acrylate monomer resin, epoxy monomer resin, carbonate monomer resin, or combinations thereof.

For instance, suitable acrylate monomer resins are methacrylate monomer resin, cyanoacrylate monomer resin, methylmethacrylate monomer resin, hydroxy ethyl methylmethacrylate monomer resin, or combinations thereof. Especially suitable as the acrylate is a resin that is an adduct of bis-phenol A and gycidyl dimethacrylate or a resin that is triethylene glycol dimethacrylate or a blend of these two resins.

The monomer resin contains a polymerization initiator that is suitable for the particular monomer resin being formed into a polymer, the particular initiator that works for a particular monomer resin being known to those skilled in the art. Several polymerization initiators are commercially available, and suitable ones include, but are not limited to, benzoin ethyl ether, benzoin methyl ether, and camphorquinone. Other typical ingredients, such as coupling agents, primer agents, and/or sizing agents, as well known in the art of polymer chemistry, may also be present.

The term "polymer" as used herein generally includes, but is not limited to, homopolymers, copolymers, such as, for example block, graft, random and alternating copolymers, terpolymers, et cetera, and blends and modifications thereof. Furthermore, the term "polymer" shall include all possible molecular configurations of the material. These structures include, but are not limited to isotactic, syndiotactic and random molecular configurations, whether linear or crosslinked.

Furthermore, depending on the choice of fiber and monomer for the resultant composite profile of fiber and plastic, the profile can be wholly or partially absorbable, non-absorbable, dissolvable, biodegradable, oxidizable, et cetera.

The radiation may be selected from the group consisting of infra-red rays, visible rays, ultraviolet rays, x-rays, gamma rays, beta particles, high energy electrons, or combinations thereof. Appropriate sources of radiation are commercially available.

The pultrusion apparatus comprises a rack component, a bundle spreader component, a forming die component with curing chamber component therein, and a winder component. Various kinds of metals and metal alloys, such as iron, copper, or aluminum are suitable for the manufacture of these components of the pultrusion apparatus, as well as ceramic materials, such as quartz, alumina, zirconia, or investment stone.

Preferably, the pultrusion apparatus is vertically disposed so that the fiber(s) move(s) vertically from top to bottom through the apparatus as the pultrusion procedure is conducted. Thus, the rack holding the at least one spool of fiber should be disposed at the top thereof; the bundle spreader should be disposed below the rack and the at least one spool of fiber; the forming die should be disposed below the bundle spreader; and the winder should be disposed below the forming die.

Although it is not intended to be bound to any theory, it is believed that the preferred vertical arrangement of the pultrusion apparatus utilizes the influence of gravity to promote radially symmetric pressure such that when a plurality of fibers is employed, the fibers tend to migrate toward the outside of the profile. Migration toward the outside of the profile of FRP can be seen in the photomicrographs of the cross-sections of the various profiles in FIG. 6, as discussed below in greater detail. Of course, the pultrusion apparatus could be disposed at an angle off vertical, such as 10°, 20°, and the like, including being horizontally disposed (90° off vertical), but the resultant characteristics of the profile could change as radially symmetric pressure may not be obtained.

The resultant profile of pultruded product has a high tensile strength, which, in the preferred embodiment, is comparable to that of a similarly sized steel wire. The tensile strength of any particular pultruded product depends on whether it has been manufactured with one fiber or a plurality of fibers, the tensile strength generally increasing with the increased loading of fibers, as loading (the number of spools of fiber and thus the number of fibers used with the pultrusion apparatus) can vary.

With the fiber used being a bundle of filaments as illustrated in the examples below, loading typically may vary from 1 to 20 spools and therefore from 1 to 20 fibers, or even more, with from 2 fibers to 20 fibers being suitable and from 4 fibers to 18 fibers being very suitable for those profiles described in the examples. Of course, loading can be much higher, with thousands of fibers, especially if each fiber is an individual filament. Also, whether fiber that is a bundle, fiber that is an individual filament, or a combination thereof is employed, different kinds of the fiber materials, as noted above, can be employed. Thus, what is an important feature of the present invention is the percent volume of fiber reinforcement in the profile, not the particular number of fibers loaded into the profile, and so thin pultruded fiber-reinforced plastic containing from about 9% to about 91% by volume of polymeric plastic and from about 91% to about 9% by volume fiber may be manufactured.

As the fiber(s) enter(s) the bundle spreader, the bundle spreader spreads each fiber to facilitate impregnation (wetting) of each fiber with a polymerizable monomer resin, preferably a photo-polymerizable monomer resin, contained inside the bundle spreader. Suitably, the resin is fed into the top of the bundle spreader with an automatic feeder, but in the examples below was fed manually.

As wetted fiber is pulled through the forming die, it is shaped into a profile. In other words, a funnel at the mouth of the forming die forms the wetted fiber so that the profile will have a predetermined resultant cross-sectional morphology, depending on the intended end use of the pultruded product, as the profile of FRP exits the bottom of the curing chamber. After forming, the monomer resin, with which the fiber is wetted, is cured in the curing chamber portion of the forming die by the radiation.

The profile may have any predetermined cross-sectional morphology, and may be symmetrical or asymmetrical. The cross-sectional morphology generally ranges from an essentially circular cross-sectional morphology to an essentially rectangular cross-sectional morphology and may be any shape in between. Suitable cross-sectional morphologies include, but are not limited to, square, elliptical, rhomboid, hexagonal, octagonal, rectangular, circular, and combinations thereof. Preferably, the profile has a cross-sectional morphology that is essentially circular and ranges from about 0.010 to about 0.030 inch (about 0.025 cm to 0.076 cm) in diameter, more preferably from about 0.012 to about 0.025 inch (about 0.030 cm to about 0.063 cm) in diameter.

As noted above, the profile may be further shaped, which is colloquially referred to as beta-staging. This may be accomplished with heat, but can be achieved by first only partially curing the resin when making the pultruded fiber-reinforced plastic product, and then beta-staging to change the shape of the profile, to finish the curing, or a combination thereof. Thus, the term "curing" as used herein in reference to curing of the resin while the wetted fiber is in the curing chamber, is intended to mean total curing or partial curing, whereby the resin may be, respectively, completely polymerized or partially polymerized.

Also, for controlling the speed of the fiber(s) being pulled through the pultrusion apparatus and for controlling the intensity and timing of the radiation, the apparatus may suitably be connected to a commercially available computer. Optionally, the computer may have software with algorithms to permit the FRP to be beta-staged at a constant speed, even though the winder may have been designed with a non-circular cross-section.

As the level of volume % reinforcement with fiber increases, the mechanical properties change. In other words, the strength (tensile strength) and the stiffness (elastic flexure modulus) of the resultant pultruded composite of plastic and fiber generally increase. Additionally, the elastic modulus of tension and flexure strength will generally increase, as the level of volume % reinforcement with fiber increases.

For a typical composite having about 62 to 66% reinforcement of quartz fibers, wherein the fiber used was a bundle of filaments, of the preferred embodiment of pultruded profile of quartz fiber-reinforced methacrylate copolymer as per the examples below, exemplary data were E=about $6 \times 10^6$ psi to $6.5 \times 10^6$ psi (about $4.2 \times 10^{10}$ Pa to $4.5 \times 10^{10}$ Pa), σ=about $2.7 \times 10^5$ psi to $3.2 \times 10^5$ psi (about $1.8 \times 10^9$ Pa to $2.2 \times 10^9$ Pa), and water absorption=1.5%, wherein E represents the elastic flexure modulus and σ represents strength (tensile strength of how much pulling force per cross-sectional area is necessary to apply to the fiber-reinforced plastic until it breaks into two).

Furthermore, it is noted that a tensile strength of about $3 \times 10^5$ psi, about in the middle of the range of $2.7 \times 10^5$ psi to $3.2 \times 10^5$ psi mentioned in the above paragraph, (about $2 \times 10^9$ Pa, about in the middle of the range of $1.8 \times 10^9$ Pa to $2.2 \times 10^9$ Pa mentioned in the above paragraph) is comparable to that of similarly sized steel wire used for orthodontic wires and face bows, which will typically have a tensile strength of about $3 \times 10^5$ psi (about $2 \times 10^9$ Pa). Steel wire can be manufactured to have a tensile strength up to about $5 \times 10^5$ psi (about $3 \times 10^9$ Pa). However, for orthodontic wires and face bows, it is not necessary for the steel wire to have a tensile strength of about $5 \times 10^5$ psi (about $3 \times 10^9$ Pa), as steel wire with a tensile strength of about $3 \times 10^5$ psi (about $2 \times 10^9$ Pa) is sufficiently strong. In connection therewith, it is noted that the FRP of the present invention has been made with a tensile strength of about $3.9 \times 10^5$ psi (about $2.7 \times 10^9$ Pa). (See laboratory data below vis-a-vis the composite that was about 79.3% by volume reinforced with S2 glass fiber.)

Therefore, by the phrase that the inventive profile has a "tensile strength comparable to similarly sized steel wire" as used herein, it is meant that, in the preferred embodiment, the inventive profile has a sufficient strength so that it may be used instead of steel wire as an orthodontic wire or face bow.

It is further noted that orthodontic wires and face bows should have certain force versus deflection characteristics (1) in order to move teeth slowly without hurting the patient and (2) in order to tighten the wires about every 2 weeks rather than every day or two. Deflection is related to how much the profile can be deflected or stretched longitudinally and still return to its original size instead of being permanently elongated. For a given orthodontic force and wire diameter, deflection is directly proportional to flexure modulus. FRPs having a flexure modulus from about $2.5 \times 10^6$ to about $8.2 \times 10^6$ psi (from about $1.7 \times 10^{10}$ Pa to about $6.0 \times 10^{10}$ Pa) and a tensile strength from about $1.1 \times 10^5$ psi to about $3.9 \times 10^5$ psi (from about $0.77 \times 10^9$ Pa to about $2.6 \times 10^9$ Pa) are suitable for use as an orthodontic wire or face bow.

Therefore, in the preferred embodiment of pultruded composite of methacrylate copolymer reinforced with about 62 to 66% by volume of quartz fibers made as described below, the flexure modulus and tensile strength of E=about $6 \times 10^6$ psi (about $4.2 \times 10^{10}$ Pa) and σ=about $3 \times 10^5$ psi (about $2 \times 10^9$ Pa), respectively, are very suitable for use of the preferred FRP as an orthodontic wire or face bow.

Moreover, the inventive preferred embodiment of the FRP had a color that closely matched that of a natural tooth. Thus, use of the resultant product as an orthodontic wire or orthodontic face bow in place of the presently used steel wire will provide not only the necessary strength and deflection for moving teeth, but also will provide good aesthetics.

Although in the preferred embodiment, the profile of pultruded reinforced fiber is intended to be used as an orthodontic arch wire or an orthodontic face bow, various other uses are contemplated for the product. For instance, the profiles could be used to make sutures or to make bone plates for fracture repair surgery and/or for hip/rib replacement surgery. Additionally, the profiles could be used in the manufacture of medical products, such as periodontal drug-pultruded rope, von Frey hairs for neurophysiological measurements, miniature probes for diagnosis and surgery, needles, and implantable strips for dispensing a prescribed dose of drugs to targeted areas in the body. Also, the profiles would be suitable in the manufacture of any products needing high stiffness and/or high strength, for instance, construction products, such as airplanes, automobiles, aerospace products, bridges, buildings (including walls, door panels, and other components thereof), concrete, earthen reinforcement webbing (useful in dams, road embankments, mining shafts, and the like), bullet-proof vests, window frames, and shelving struts.

Furthermore, several profiles, for instance, 2 to 1000, or even more, could be associated or aggregated together to make a bigger profile, like twined rope and/or like woven fabric, and the aggregate could be employed in making any one or more of the just mentioned products. But in particular, the aggregate would be useful in the manufacture of orthodontic brackets, improved reinforced plaster of Paris to augment alveolar bone loss, casts to set broken limbs, bone fixation plates for fracture repair, artificial bones with varying stiffnesses and mechanical properties mimicking cancellous or cortical bones, and internal screens and webbing for surgical repairs.

DEFINITIONS

For clarity, the following definitions employed throughout the specification are repeated here.

As used herein, the terms "fiber-reinforced plastic" and "fiber-reinforced composite" are interchangeable and both are intended to refer to the resultant pultruded product of polymeric plastic and fiber. In general, the pultruded product is referred to herein as a profile of pultruded fiber-reinforced plastic, which, for simplicity is abbreviated as FRP.

Specifically as used herein with respect to the present invention, the term "fiber" is intended to mean a bundle of individual filaments and also to include in the meaning one filament. Thus, in addition to the resultant pultruded product of the instant invention being a composite of plastic and fiber, wherein each fiber is a "bundle" of filaments as per the profiles that were made, conceivably, the resultant pultruded product of the instant invention could be a composite of polymeric plastic and fiber, wherein each fiber is one filament. Also, the resultant pultruded product of the instant invention could be a composite of polymeric plastic, wherein the fiber is a combination of bundle(s) and filament(s).

The term "polymer" as used herein generally includes, but is not limited to, homopolymers, copolymers, such as, for example block, graft, random and alternating copolymers, terpolymers, et cetera, and blends and modifications thereof. Furthermore, the term "polymer" shall include all possible molecular configurations of the material. These structures include, but are not limited to isotactic, syndiotactic and random molecular configurations, whether linear or cross-linked.

As used herein, the term "beta-staging" is intended to refer to further shaping of a profile of pultruded fiber-reinforced plastic product in the longitudinal direction, in the cross-sectional direction, or in a combination thereof, by putting the product through additional dies, rollers, and the like, to change the overall conformation of the product. Beta-staging is usually accomplished with heat, but can be achieved by first only partially curing the resin when making the pultruded fiber-reinforced plastic product, and then beta-staging to change the shape, followed by completing the curing so that the change in shape is stabilized. Also, beta-staging can include coating the product or implanting a finish thereon.

Thus, the term "curing" as used herein in reference to curing of the resin while the wetted fiber is in the curing chamber, is intended to mean total curing or partial curing. Hence, the pultruded product may have the resin partially polymerized or completely polymerized.

By the phrase that the inventive profile has a "tensile strength comparable to similarly sized steel wire" as used herein, it is meant that, in the preferred embodiment, the inventive profile has a sufficient strength so that it may be used instead of steel wire as an orthodontic wire or face bow.

Discussion of the Preferred Embodiments and of the Figures

More particularly, with regard to the apparatus and components thereof depicted in FIGS. 1–5, profiles of pultruded quartz fiber-reinforced methacrylate copolymer, as depicted in FIG. 6, were made as follows. It is noted that the same numerals refer to the same components in the various Figures.

Figure 2:
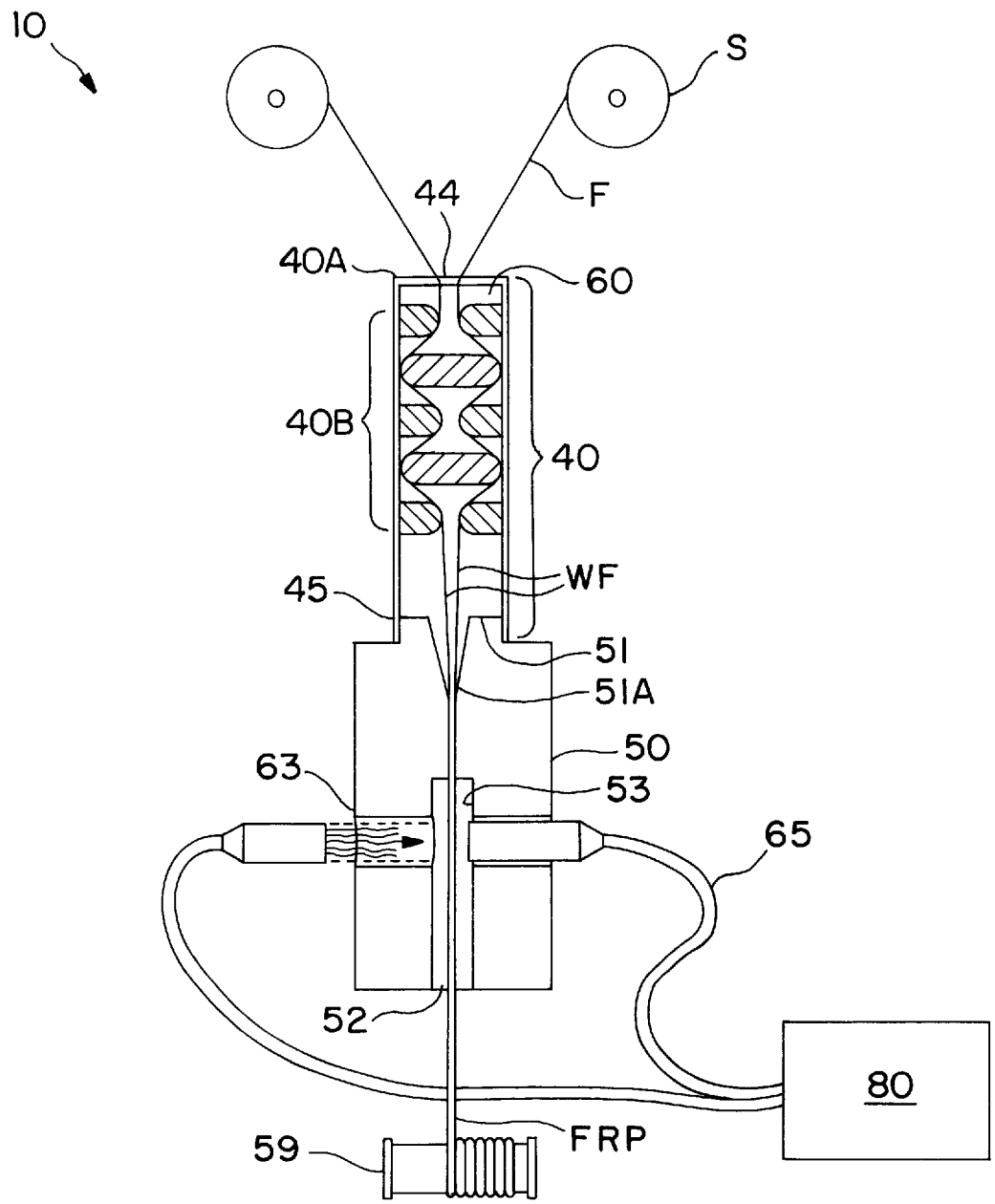
FIG. 2 is a side view in cross-section of the pultrusion apparatus of FIG. 1, with support structure removed.
Figure 3:
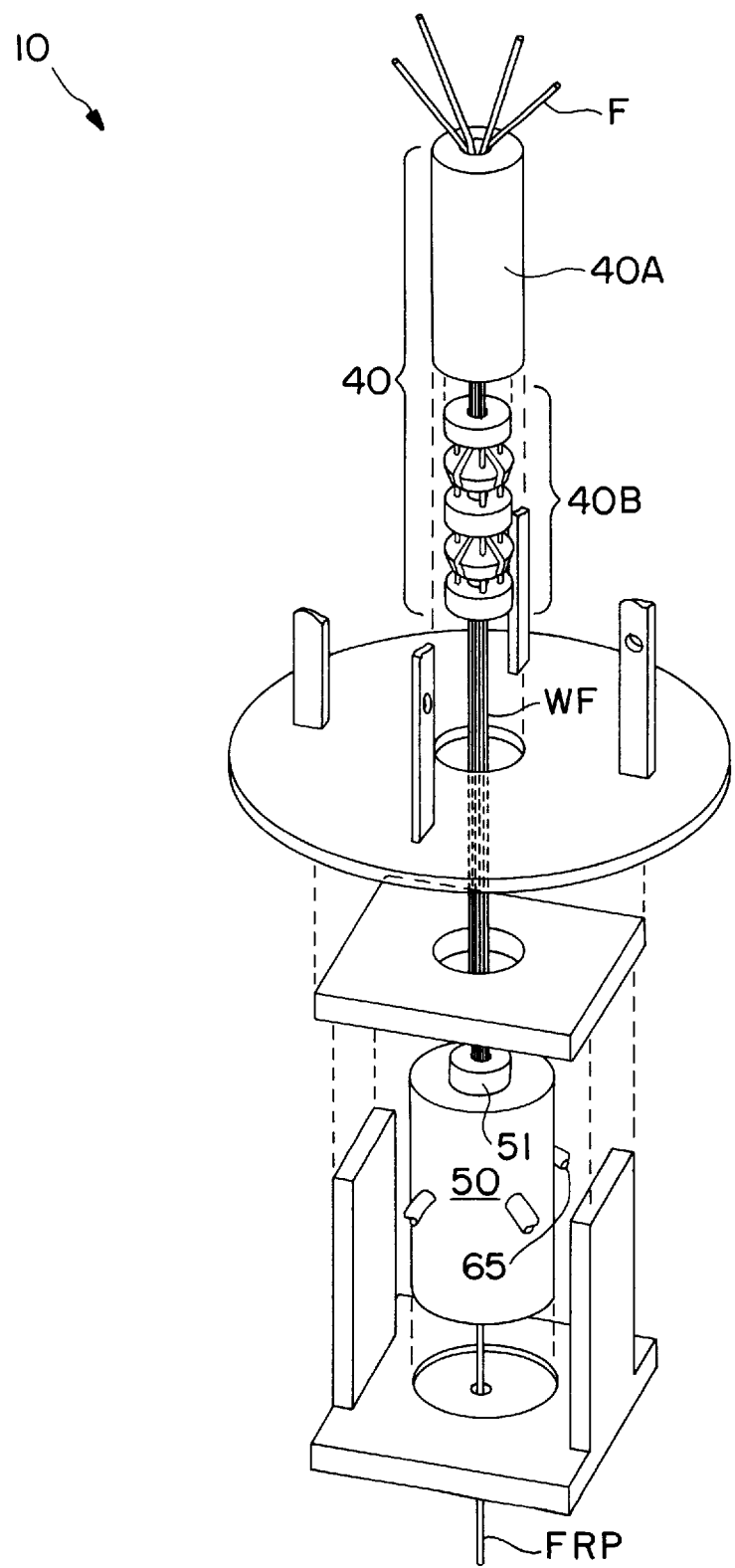
FIG. 3 is an exploded perspective view of the pultrusion apparatus of FIG. 1, with the cover of the bundle spreader component of the apparatus separated and above the bundle spreader device component whereby this component can be seen above the forming die component of the apparatus.

Specifically with regard to FIGS. 1–3, generally shown is pultrusion apparatus 10 having a plurality of spools S of fiber F placed on rack 30, to hold 1 or more spools S disposed above bundle spreader 40, which in turn is disposed above forming die 50. Suitably, rack 30 is a creel. For the pultrusion apparatus 10 constructed, from the top of spools S to the bottom of curing chamber 50 was about 16 inches (41 cm) and apparatus 10 was about 6 inches (15 cm) across.

It is noted that although the Figures illustrate the preferred embodiment of pultrusion apparatus 10 being vertically disposed, as indicated above, pultrusion apparatus 10 may be disposed at any angle off vertical, even so that it is horizontally disposed, for instance, from about 1° to about 90°.

Furthermore, even though the Figures, for convenience, illustrate 4 spools S and therefore 4 fibers F on rack 30, loading may vary from 1 to 20 spools S and therefore from 1 to 20 fibers F, or even more, when fiber that is a bundle is employed. When fiber that is a filament is employed, loading may be up in the thousands. Nevertheless, as noted above, the important feature of the present invention is the volume % fiber reinforcement, and thus how many spools are employed will be determined by the kind of fiber and the resultant desired volume % of fiber reinforcement in the pultruded product. Hence, thin pultruded fiber-reinforced plastic containing from about 9% to about 91% by volume of polymeric plastic and from about 91% to about 9% by volume fiber may be manufactured.

For the preferred embodiment, employed were spools of quartz fiber, wherein each spool contained a bundle of approximately 120 filaments, obtained from Quartz Products Company of Louisville, Ky., and the particular quartz fiber employed was approximately 9 μm in diameter.

It is generally noted that bundle spreader 40 has entrance 44 and exit 45 for movement of fiber F therethrough. Details of movement of fiber F through bundle spreader 40 are discussed below vis-a-vis FIGS. 4 and 5. Forming die 50 has a channel therein with entrance 51 and exit 52 for movement of fiber F therethrough. Spreader exit 45 is operatively associated with entrance 51, and preferably is adjacently connected thereto. Also, forming die 50 has curing chamber 53 therein. Hence, as can be seen, fiber F moves from spools S, through bundle spreader 40, and then through forming die 50 and curing chamber 53 therein.

Since in the preferred embodiment, pultrusion apparatus 10 is vertically disposed, this movement of fiber F is vertically downwards, and more preferably, there are a plurality of fibers F so that this movement should be also symmetrical about the central vertical axis of pultrusion apparatus 10.

More particularly, fiber F was inserted into entrance 44 of bundle spreader 40, which had a bath of monomer resin 60 which was fed inside thereof. As fiber F was pulled, preferably vertically, through bundle spreader 40 of pultrusion apparatus 10, the components (shown in more detail in FIGS. 4 and 5 discussed further below) of bundle spreader 40 spread each fiber F as each fiber F was concurrently wetted with monomer resin 60, and therefore exited from exit 45 of bundle spreader 40 as wetted fiber WF, wetted with monomer resin 60.

Then, wetted fiber WF was inserted into forming die 50 via entrance 51 thereof, passed through curing chamber 53, and then brought out exit 52 at the bottom thereof as a profile of cured pultruded fiber-reinforced plastic FRP. Curing chamber 53 contained argon as an inert gas to obviate wetted fiber WF becoming tacky while therein. Other suitable gases, that curing chamber 53 may contain in order to obviate wetted fiber WF from becoming tacky or facilitate other chemical reactions therein, include, but are not limited to, such reactive or inert gases as nitrogen, hydrogen, ammonia, helium, neon, or combinations thereof.

As can be better seen in FIGS. 2 and 3, a bath of monomer resin 60 was manually placed inside of bundle spreader 40 prior to inserting fiber F therein, and cover 40A of bundle spreader 40 suitably retained monomer resin 60 inside of bundle spreader 40. Specifically due to the exploded view in FIG. 3, wherein cover 40A is shown separated from inner workings 40B of bundle spreader 40, the relationship of cover 40A and inner workings 40B to each other can be seen.

In the preferred embodiment, the particular monomer resin 60 employed was an acrylate monomer that was a blend of (1) an adduct of bis-phenol A and gycidyl dimethacrylate and (2) triethylene glycol dimethacrylate, available from Polysciences of Warrington, Pa. The monomer resin contained benzoin ethyl ether as the polymerization initiator in order to trigger the polymerization reaction. Curing was total so that the resin was completely polymerized. Acrylate monomer that is a blend of (1) and (2) is a very suitable resin to employ as it has an affinity for the treated surface of quartz fiber. As noted, the plastic and fiber should be adhered or bonded together in the pultruded product.

Forming die 50 was suitably attached via 4 window apertures 63 disposed on the sides thereof to a fiber-optic cable furcated into four "hydras" 65, each of which in turn was attached to radiation source 80. It is noted there could be from 1 aperture 63 up to 12 apertures 63, or more. For the preferred embodiment, radiation source 80 was suitably an ultraviolet (hereinafter, abbreviated as UV) ray source, namely a DURALUX UV-300 that had been obtained from Kulzer of Bad Homburg, West Germany. The number of apertures 63 and the number of fiber-optic cables 65 corresponded one to one. Source 80 was activated and thereby provided ultraviolet light in an amount of 300 watts to initiate the polymerization reaction in monomer resin 60, thereby providing curing.

Although window apertures 63 were open slots, they may suitably be made of quartz for when radiation source 80 is UV. Of course, the amount of radiation and the window material, if any, will vary depending on the particular radiation source chosen, as is known to those skilled in the art.

As the curing was taking place, and monomer resin 60 with which fiber F was wetted formed a polymeric plastic, entrance aperture 51 of the forming die 50, suitably in the shape of a funnel having a neck or bore 51A with a generally circular cross-section (i.e., the neck 51A was a truncated cone), formed the material into a shaped profile so that cured pultruded FRP exited from exit 52 of forming die 50 with a cross-sectional morphology that was essentially circular.

The cross-sectional morphology of the profile of cured pultruded fiber-reinforced plastic FRP may be of any shape, including asymmetrical as well as symmetrical, and can be easily predetermined by the person of ordinary skill in the art by choosing funnel neck 51A with an appropriate cross-sectional design. Typically, the cross-sectional morphology will range from generally circular to generally rectangular. For instance, if the cross-section of the funnel neck 51A is circular, the profile FRP will be of a predetermined circular morphology. Besides circular and rectangular, other suitable cross-sectional designs for funnel neck 51A include, but are not limited to, square, elliptical, rhomboid, hexagonal, octagonal, and combinations thereof.

As the profile of cured pultruded fiber-reinforced plastic FRP exited from exit 52 of forming die 50, winding element 59 to which profile FRP was attached, wherein winding element 59 suitably is a motor-driven drum or wheel, exerted a pulling force on profile FRP as profile FRP was collected thereon. The rate and intensity, and thus the extent, of the polymerization reaction was controlled indirectly by varying the pulling speed via winder 59 and thereby determining the residency time of wetted fiber WF inside of UV chamber 53.

Therefore, varying the pulling speed would also affect the morphology of profile FRP. More specifically, winder 59 is shown in its preferred embodiment with a generally cylindrical shape, and thus with a generally circular cross-section, but it could be shaped with various geometries. The shape of winder 59, together with variance of the pulling speed thereof, additionally can provide various longitudinal conformational changes for the morphology of profile FRP, in addition to the transverse cross-sectional shaping provided generally by the shape of funnel neck 51A, so that in the longitudinal direction fiber-reinforced plastic FRP can be made straight, bent, or curved, as desired. In other words, beta-staging of profile FRP vis-a-vis partial curing may be effected by variance of the pulling speed of winder 59, together with conformational change of profile FRP when winding it on winder 59, and then profile FRP would be finally cured.

Of course, profile FRP may be further beta-staged to additionally change the morphology longitudinally, in the cross-sectional direction, or a combination thereof. Hence, these permutations of the speed and shape of winder 59 can be designed also to affect the beta-staging of profile FRP, as well as conducting the beta-staging in ways noted above.

Winder 59 and radiation source 80 were connected to a computer (not shown) to provide control of pulling speed. If desired, the amount and timing of the radiation emitting from radiation source 80 may also be controlled. Such computer technology is quite common today, and obviates the inconvenience of a worker having to provide the control manually.

Figure 4:
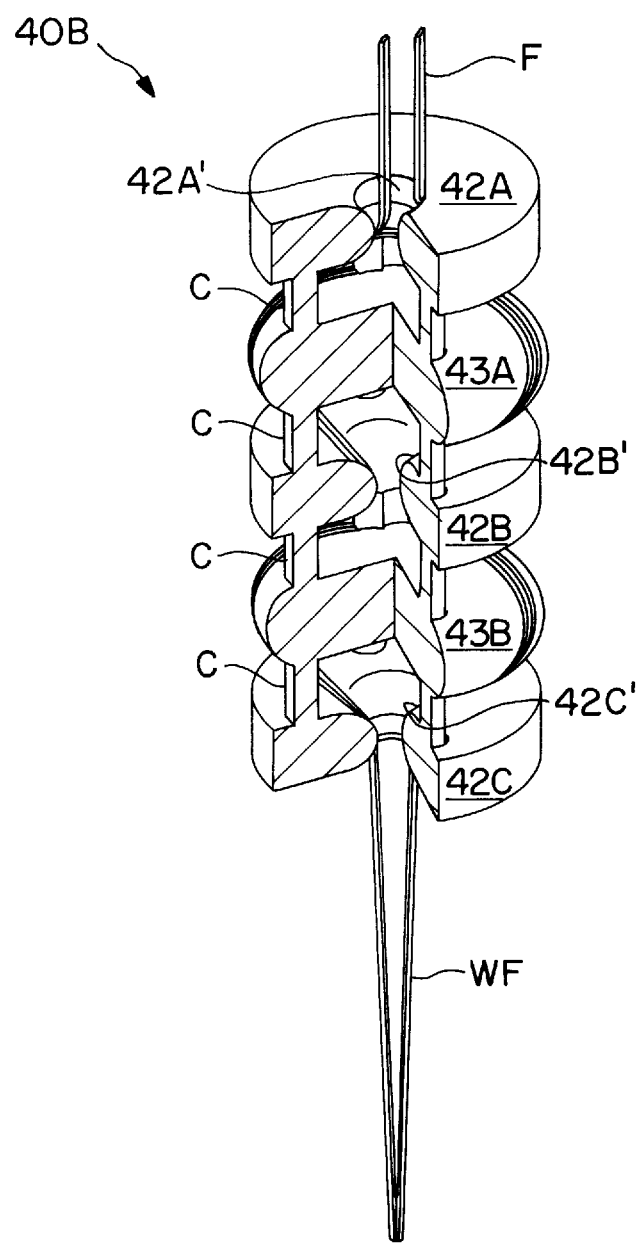
FIG. 4 is a perspective view in partial cutaway of the bundle spreader component of the pultrusion apparatus of FIG. 3.
Figure 5:
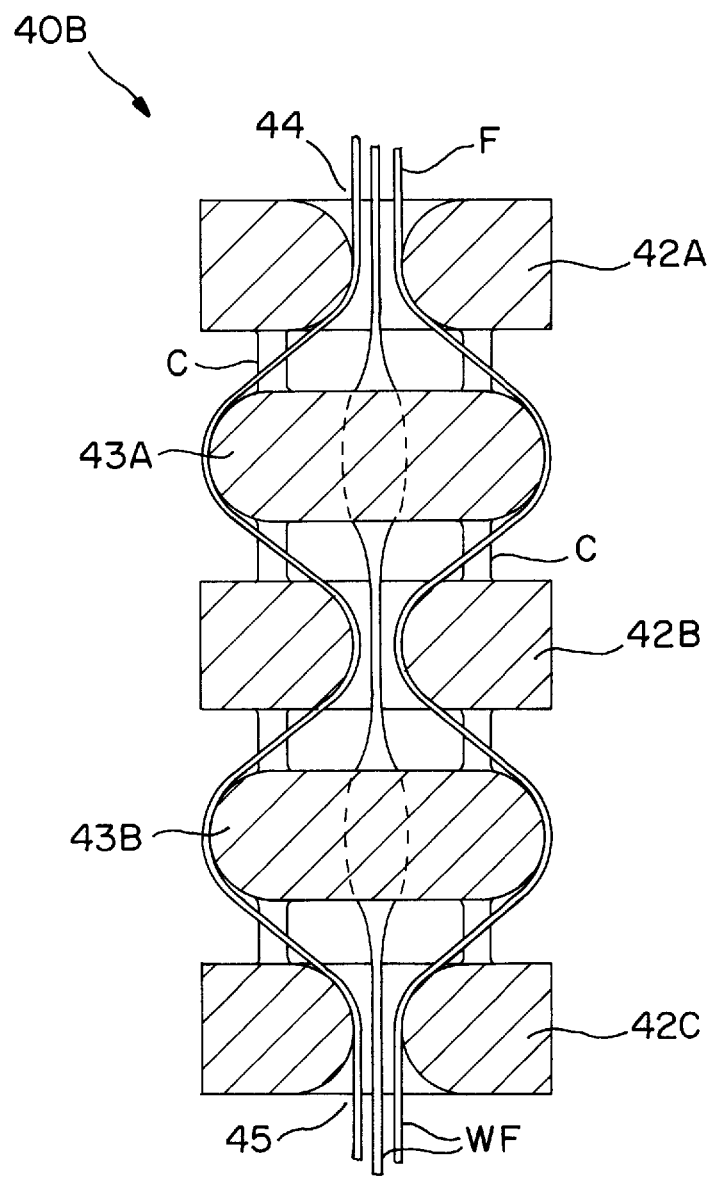
FIG. 5 is a side view in cross-section of the bundle spreader component of FIG. 4.
Figure 6A:
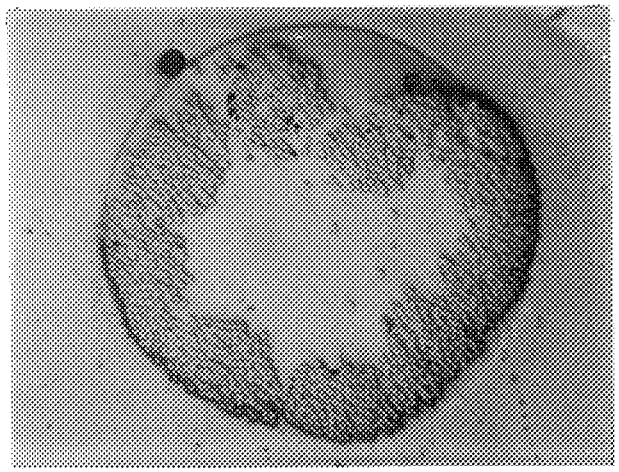
FIG. 6 is six photographs taken through a microscope and thus enlarged (actual size is approximately 500 μm) of profiles of pultruded fiber-reinforced plastic with various amounts of reinforcement.
Figure 6B:
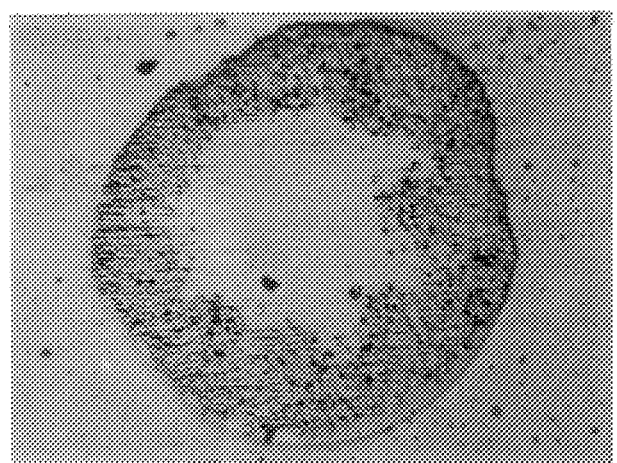
Figure 6C:
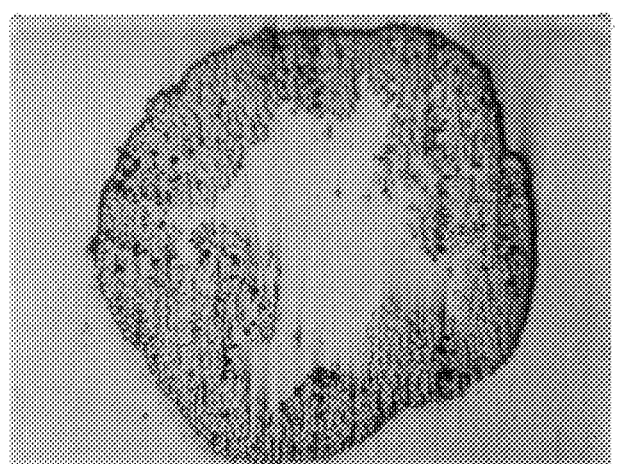
Figure 6D:
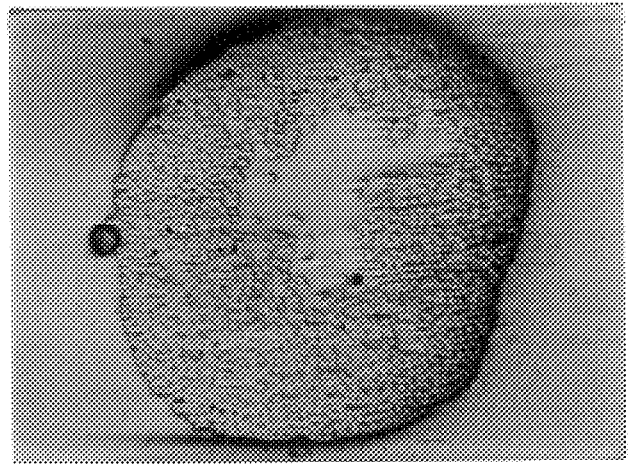
Figure 6E:
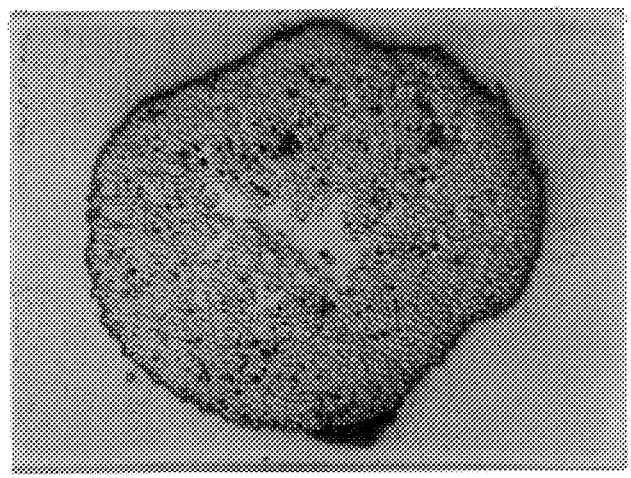
Figure 6F:
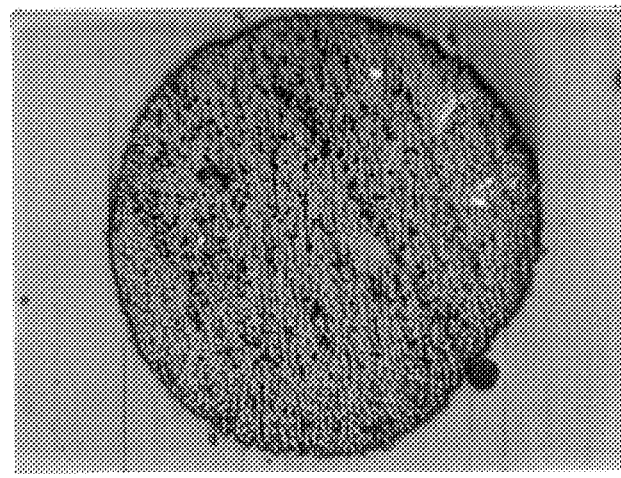

With particular regard to FIGS. 4 and 5, greater detail of the components of bundle spreader 40 can be seen. Not only is cover 40A of bundle spreader 40 removed to afford a view of inner workings 40B of bundle spreader 40, but also inner workings 40B are shown in both cutaway (FIG. 4) and cross-section (FIG. 5). As discussed above, cover 40A is employed to contain monomer resin 60 inside of bundle spreader 40 as fiber F is pulled therethrough and concurrently wetted with resin 60.

More specifically, inner workings 40B of bundle spreader 40 comprise a series of alternating disks 42 and cams 43. Whatever alternating sequence of disks 42 and cams 43 is employed, it is important that the sequence begin with and end with a disk 42. Thus, the number of disks is always 1 more than the number of cams. There must be at least 2 disks 42 and 1 cam 43, and depending on the thickness of the fiber F used and/or the size of disks 42 and cams 43, there could be up to 20 disks 42 and 19 cams 43, or even more.

For each pair of adjacent disks 42 and cams 43, disk 42 and cam 43 of the pair are operatively associated with each other, and preferably should be rigidly connected to each other via at least one connector C. Suitably, there are 4 connectors C connecting each pair of adjacent disks 42 and cams 43. In the preferred embodiment illustrated in FIGS. 4 and 5, there are 3 disks 42 and 2 cams 43 in the following series order, disk 42A, cam 43A, disk 42B, cam 43B, and disk 42C, with 4 connectors C connecting each adjacent pair.

Each disk 42 is provided with an aperture therethrough, preferably disposed in the center thereof, and indicated in FIGS. 4 and 5 are aperture 42A', aperture 42B', and aperture 42C', disposed, respectively, in the center of disks 42A, 42B, and 42C. Preferably, as illustrated in FIGS. 4 and 5, the apertures are generally circular in the horizontal cross-sectional direction and the inside surfaces of the aperture portions of the disks are rounded so that the apertures are generally elliptical hyperboloid or generally elliptical paraboloid in the vertical cross-section.

Fiber F is inserted into bundle spreader entrance 44 and fed through aperture 42A'. (Entrance 44 and aperture 42A' coincide.) As fiber F comes out of aperture 42A' and exits from the bottom of disk 42A, it then comes over and around cam 43A and next enters aperture 42B'. After exiting aperture 42B' at the bottom of disk 42B, it then comes over and around cam 43B and next enters aperture 42C'. By fiber F coming over and around cams 43A and 43B, each fiber F spreads whereby it can become better impregnated with resin 60 that is inside of bundle spreader 40 so that it exits from exit 45 of bundle spreader 40 as wetted fiber WF and then enters funnel entrance 51 of forming die 50. As noted, monomer resin 60 is cured in curing chamber 53 to form the polymer, and winder 59 pulls profile of pultruded fiber-reinforced plastic FRP out of exit 52 of forming die 50, and collects product FRP thereon.

Although the following is depicted in the preferred embodiment in FIGS. 4 and 5, it is not intended to be limited thereby, and other embodiments are contemplated as being within the scope of the invention. More particularly, the disks 42 are all the same size and the cams 43 are all the same size, and the disks 42 and cams 43 are all vertically aligned. Also, the apertures 42' are all the same size, circular, and in the center of the respective disks, and the cams 43 are all circular in horizontal cross-section. As a result, for the preferred embodiment depicted in FIGS. 4 and 5, if one looks down from the top of bundle spreader 40, the apertures of the disks and the circumferences of the cams form aligned coaxial arches. Of course, if desired, not only could the alignment be off so that the apertures of the disks and the circumferences of the cams are not coaxial, but also the cams could be different sizes and/or shapes, the disks could be different sizes and/or shapes, and the apertures could be different sizes and/or shapes. Thus, the apertures of the disks and the circumferences of the cams form aligned coaxial arches, such that the individual filaments in a bundle of a fiber are spread out equidistantly around the circumference of each cam to reduce strain on each filament and to facilitate wetting by the monomer.

The procedure was repeated to manufacture profiles with various % volume levels of quartz fiber reinforcement. Meantime, the pulling speed was maintained at 0.05 inch/second (0.127 cm/second) for all profiles, and the outside diameters were maintained at 0.020 inches (0.050 cm) for all profiles. Suitable cross-sectional diameters may range from about 0.010 to about 0.060 inch (about 0.025 to about 0.152 cm) in diameter, particularly when it is intended to use the FRP as an orthodontic wire or face bow.

With regard to FIG. 6, shown are 6 photomicrographs of the cross-sections of 6 profiles of the FRPs made of quartz and polymerized methacrylate monomer, as described above. As the cross-sections were photographed through a microscope, they are thus enlarged (actual size is approximately 500 $\mu$m). Due to the enlargement, from the first photomicrograph with 35% by volume fiber reinforcement of the profile, it can be seen in that the quartz fibers were bundles of filaments.

The 6 profiles were manufactured, respectively, with a plurality of 9 fibers (35% by volume fiber reinforcement), 10 fibers (39% by volume fiber reinforcement), 12 fibers (47% by volume fiber reinforcement), 14 fibers (54% by volume fiber reinforcement), 16 fibers (62% by volume fiber reinforcement), and 18 fibers (70% by volume fiber reinforcement), and thus with 9 spools S, 10 spools S, 12 spools S, 14 spools S, 16 spools S, and 18 spools S, respectively, as indicated by each photomicrograph in FIG. 6. (Other selected % volume reinforcement levels were made but photomicrographs of cross-sections thereof are not shown in FIG. 6.) Of course, depending on the fiber chosen, the number of fibers for any particular % volume reinforcement will vary.

It is noted that, when a plurality of fibers was employed during manufacture of the profile, the fibers appear to be forced to migrate toward the outer boundary of the profile, as can be seen in the 6 photomicrographs of the cross-sectional morphology of the 6 various reinforcement levels, and especially can be seen with the 35% by volume reinforcement level.

Figure 7B:
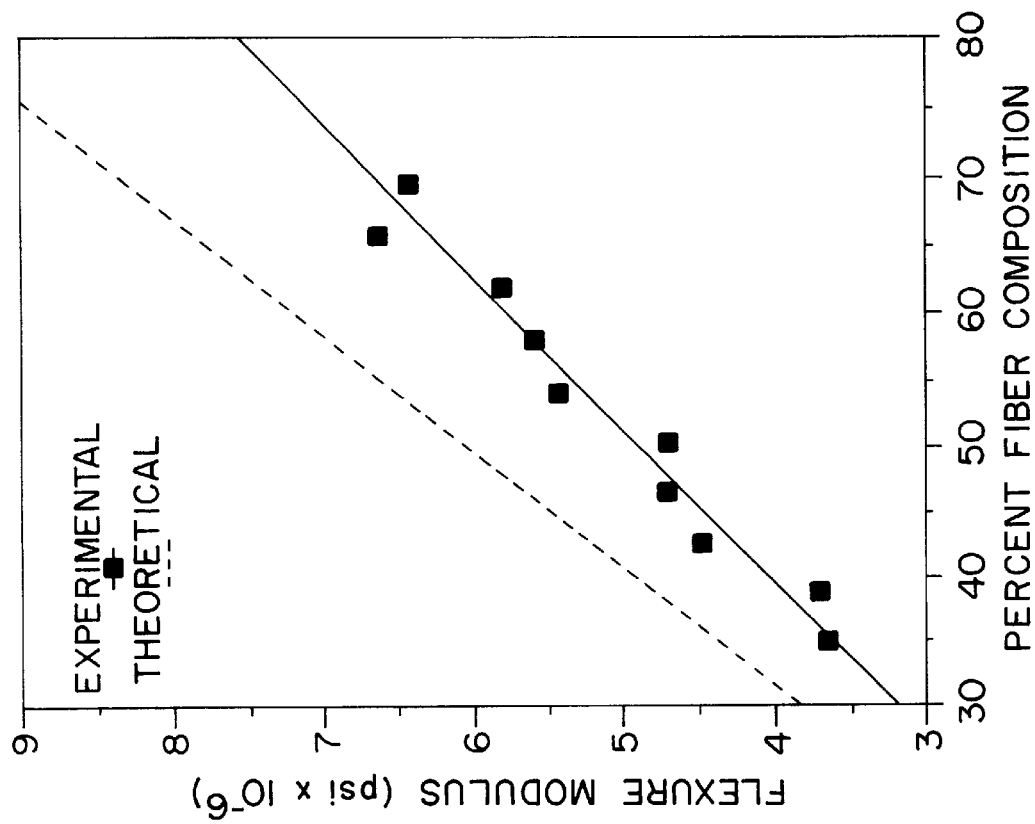
FIG. 7 is two graphs, the left one showing the tensile strength and the right one showing the flexure modulus, of profiles of pultruded fiber-reinforced plastic with various amounts for reinforcement.
Figure 7A:
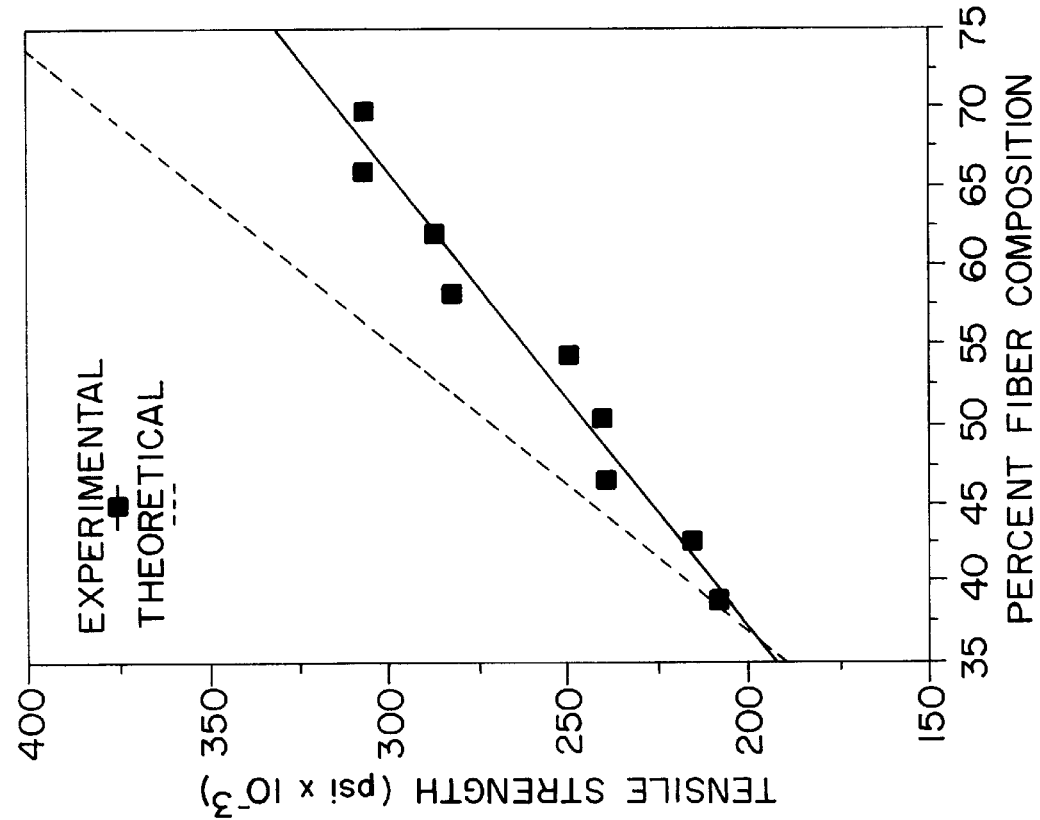

FIG. 7 shows 2 graphs depicting properties of FRPs made. More specifically, the tensile strength as compared to % fiber composition by volume is depicted in the left-side graph (for the various % volume reinforcement levels with quartz fiber), and the flexure modulus as compared to % fiber composition by volume is depicted in the right-side graph (for the various % volume reinforcement levels with quartz fibers). In connection with these graphs, it can be seen that as the level of quartz fibers increased from 30% to 70% by volume, the resultant fiber-reinforced composite generally increased in tensile strength and generally increased in stiffness (flexure modulus).

Specifically, the tensile strength ranged from about $2.2 \times 10^5$ psi (about $1.5 \times 10^9$ Pa) for a level of about 40% fiber composition by volume to a tensile strength of about $3.2 \times 10^5$ psi (about $2.2 \times 10^9$ Pa) for a level of about 70% fiber composition by volume, and the flexure modulus ranged from about $3.5 \times 10^6$ psi (about $2.4 \times 10^{10}$ Pa) for a level of about 35% fiber composition by volume to a flexure modulus of about $6.6 \times 10^6$ psi (about $4.6 \times 10^{10}$ Pa) for a level of about 70% fiber composition by volume.

Additionally, for % fiber reinforcement levels from about 33% to about 79%, the procedure was repeated with glass (both E and S2) fibers, wherein the fiber was a bundle of approximately 204 filaments, also using a monomer resin blend of (1) an adduct of bis-phenol A and gycidyl dimethacrylate and (2) triethylene glycol dimethacrylate, as was used with the quartz fibers. The spools of glass fiber were obtained from Owens-Corning Fiberglass Company of Toledo, Ohio, and the particular glass fiber employed comprised bundles having approximately 204 filaments, each filament measuring 9 μm in diameter.

Similar results of tensile strength and flexure modulus were obtained for thin profiles that ranged from about 0.012 to about 0.025 inches (about 0.030 to about 0.063 cm) in diameter, except that the tensile strength and flexure modulus were consistently somewhat higher for profiles reinforced with S-2 glass and somewhat lower for profiles reinforced with E glass, as compared to the profiles reinforced with quartz. For instance, for the profiles reinforced with S-2 fiber, the tensile strength was about $3.5 \times 10^5$ psi (about $2.4 \times 10^9$ Pa) for a volume reinforcement level of about 66%, whereas, as noted above, for the profiles reinforced with quartz, the tensile strength was somewhat lower, about $3.2 \times 10^5$ psi (about $2.2 \times 10^9$ Pa) for a somewhat higher volume reinforcement level of about 70%.

More specifically, the composites of the S-2 glass reinforced profiles ranged from a reinforcement level of about 79% by volume, which had a tensile strength of about $3.9 \times 10^5$ psi (about $2.6 \times 10^9$ Pa) and a flexure modulus of about $8.2 \times 10^6$ psi (about $5.6 \times 10^{10}$ Pa), to a reinforcement level of about 33% by volume, which had a tensile strength of about $2.1 \times 10^5$ psi (about $1.4 \times 10^9$ Pa) and a flexure modulus of about $2.9 \times 10^6$ psi (about $2.0 \times 10^{10}$ Pa). The composites of the E glass reinforced profiles ranged from a reinforcement level of about 79% by volume, which had a tensile strength of about $2.0 \times 10^5$ psi (about $1.3 \times 10^9$ Pa) and a flexure modulus of about $6.2 \times 10^6$ psi (about $4.3 \times 10^{10}$ Pa), to a reinforcement level of about 33% by volume, which had a tensile strength of about $1.1 \times 10^5$ psi (about $0.77 \times 10^9$ Pa) and a flexure modulus of about $2.5 \times 10^6$ psi (about $1.7 \times 10^{10}$ Pa).

It is noted that the composites of S-2 glass reinforced profiles for 66% by volume fiber reinforcement had a flexure modulus of $8.7 \times 10^6$ psi (about $6.0 \times 10^{10}$ Pa), which is higher than the flexure modulus of about $8.2 \times 10^6$ psi (about $5.6 \times 10^{10}$ Pa), for 79% by volume fiber reinforcement. Also, it is noted that the composites of E glass reinforced profiles for 66% by volume fiber reinforcement had a flexure modulus of $6.6 \times 10^6$ psi (about $4.5 \times 10^{10}$ Pa), which is higher than the flexure modulus of about $6.2 \times 10^6$ psi (about $4.3 \times 10^{10}$ Pa), for 79% by volume fiber reinforcement.

Of course, the particular strength and elastic flexure modulus desired will depend on the particular end use to which the profiles are put.

Both the profiles of quartz fiber-reinforced polymeric-plastic and glass fiber-reinforced polymeric-plastic should be useful as orthodontic wires and/or face bows with the orthodontic braces and/or headgear of human subjects.

It will be understood that various details of the invention may be changed without further departing from the scope of the invention. Furthermore, the foregoing description is for the purpose of illustration only, and not for the purpose of limitation—the invention being defined by the claims.

What is claimed is:

1. A profile comprising a thin pultruded fiber-reinforced plastic having (a) about 9% to about 91% by volume of polymeric plastic and about 91% to about 9% by volume fiber, (b) a diameter less than about 0.060 inch (about 0.152 cm), (c) a flexure modulus ranging from about $8.7 \times 10^6$ psi (about $6.0 \times 10^{10}$ Pa) to about $2.5 \times 10^6$ psi (about $1.7 \times 10^{10}$ Pa), and (d) a tensile strength ranging from about $3.9 \times 10^5$ psi (about $2.6 \times 10^9$ Pa) to about $1.1 \times 10^5$ psi (about $0.77 \times 10^9$ Pa), wherein said thin pultruded fiber-reinforced plastic has a tensile strength comparable to that of a similarly sized steel wire.

2. The profile of claim 1, comprising a thin pultruded fiber-reinforced plastic of about 20% to about 80% by volume of polymeric plastic and about 80% to about 20% by volume fiber.

3. The profile of claim 1, comprising a thin pultruded fiber-reinforced plastic of about 30% to about 70% by volume of polymeric plastic and about 70% to about 30% by volume fiber.

4. The profile of claim 1, wherein the fiber is selected from the group consisting of bundles, individual filaments, and combinations thereof.

5. The profile of claim 1, wherein the profile has a tensile strength ranging from about $3.2$ psi$\times 10^5$ psi (about $2.2 \times 10^9$ Pa) to about $2.2$ psi$\times 10^5$ psi (about $1.5 \times 10^9$ Pa) to and a flexure modulus ranging from about $6.6 \times 10^6$ psi (about $4.6 \times 10^{10}$ Pa) to about $3.5 \times 10^6$ psi (about $2.4 \times 10^{10}$ Pa).

6. The profile of claim 5, the profile having a tensile strength of about $3.0 \times 10^5$ psi (about $2.0 \times 10^9$ Pa) and a flexure modulus of about $6 \times 10^6$ psi (about $4 \times 10^{10}$ Pa).

7. The profile of claim 1, having a cross-sectional morphology ranging from an essentially circular cross-sectional morphology to an essentially rectangular cross-sectional morphology.

8. The profile of claim 7, having an essentially circular cross-sectional morphology with a diameter ranging from about 0.010 to about 0.030 inch (from about 0.025 cm to about 0.076 cm).

9. The profile of claim 1, wherein the polymeric plastic is formed from a radiation cured monomer resin containing a polymerization initiator suitable therefor.

10. The profile of claim 1, wherein said monomer resin is selected from the group consisting of acrylic monomer resin, acrylate monomer resin, epoxy monomer resin, carbonate monomer resin, and combinations thereof.

11. The profile of claim 10, wherein the acrylate monomer resin comprises resin selected from the group consisting of methacrylate monomer resin, cyanoacrylate monomer resin, methylmethacrylate monomer resin, hydroxy ethyl methylmethacrylate monomer resin, and combinations thereof.

12. The profile of claim 11, wherein the acrylate monomer resin comprises resin selected from the group consisting of (a) an adduct of bis-phenol A and gycidyl dimethacrylate, (b) triethylene glycol dimethacrylate, and (c) combinations thereof.

13. The profile of claim 1, wherein the fiber is selected from the group consisting of polyethylene fiber, nylon fiber, polymer fiber, glass fiber (S2 and E), graphite fiber, quartz fiber, metal fiber, ceramic fiber, boron fiber, aluminum fiber, and combinations thereof.

14. The profile of claim 9, wherein the radiation is selected from the group consisting of infra-red rays, visible rays, ultraviolet rays, x-rays, gamma rays, beta particles, high energy electrons, and combinations thereof.

15. An aggregate of a plurality of profiles wherein each profile in the aggregate comprises a thin pultruded fiber-reinforced plastic having (a) about 9% to about 91% by volume of polymeric plastic and about 91% to about 9% by volume fiber and (b) a diameter less than about 0.060 inch (about 0.152 cm).

* * * * *

UNITED STATES PATENT AND TRADEMARK OFFICE
CERTIFICATE OF CORRECTION

PATENT NO. : 5,869,178
DATED : February 9, 1999
INVENTOR(S) : Kusy, et al.

It is certified that error appears in the above-identified patent and that said Letters Patent is hereby corrected as shown below:

On the title page, item [56]

Under "Other Publications", the following publications should be included:
Jancar et al., Measurement of the Elastic Modulus of Fibre-Reinforced composites Used as Orthodontic Wires, Vol. 5, *Journal of Materials Science: Materials in Medicine*, pp. 214-218 (1994).

Goldberg et al., Screening of Matrices and Fibres for Reinforced Thermoplastics Intended for Dental Applications, Vol. 28, *Journal of Biomedical Materials Research*, pp. 167-173 (1994).

Jancar et al., Fibre-Reinforced thermoplastic composites for Dentistry, Vol. 4, *Journal of Materials Science: Materials in Medicine*, pp. 555-561 (Dec. 1993)

Signed and Sealed this

Twenty-third Day of May, 2000

Attest:

Q. TODD DICKINSON

*Attesting Officer*   *Director of Patents and Trademarks*

US005869178C1

(12) REEXAMINATION CERTIFICATE (4786th)
United States Patent
Kusy et al.

(10) Number: US 5,869,178 C1
(45) Certificate Issued: May 27, 2003

(54) PULTRUDED FIBER-REINFORCED PLASTIC AND RELATED APPARATUS AND METHOD

(75) Inventors: Robert P. Kusy, Chapel Hill, NC (US); Kenneth C. Kennedy, II, Chapel Hill, NC (US)

(73) Assignee: The University of North Carolina at Chapel Hill, Chapel Hill, NC (US)

Reexamination Request:
No. 90/005,964, Mar. 28, 2001

Reexamination Certificate for:
Patent No.: 5,869,178
Issued: Feb. 9, 1999
Appl. No.: 08/295,540
Filed: Aug. 25, 1994

Certificate of Correction issued May 23, 2000.

(51) Int. Cl.⁷ .................................................. B32B 1/00
(52) U.S. Cl. ..................... 428/335; 428/330; 428/331; 428/332; 428/333; 428/334; 428/337; 433/20; 522/908
(58) Field of Search ................................. 428/332, 333, 428/331, 334, 337, 330, 335; 433/20; 522/908

(56) References Cited

U.S. PATENT DOCUMENTS

| 4,462,946 A | 7/1984 | Goldsworthy ................ 264/23 |
| 4,717,341 A | 1/1988 | Goldberg et al. ............. 433/9 |
| 4,894,012 A | 1/1990 | Goldberg et al. ........... 433/215 |
| 5,040,964 A | 8/1991 | Oppawsky et al. ......... 425/135 |
| 5,135,685 A | 8/1992 | Masuhara et al. ........... 264/22 |

FOREIGN PATENT DOCUMENTS

GB          2214087          8/1989

OTHER PUBLICATIONS

Chin–Hsing Chen and Chen–Chi M. Ma, Journal of Applied Polymer Science, vol. 46, 937–947, "Pultruded Fiber Reinforced Blocked Polyurethane (PU) Composites. I. Processability and Mechanical Properties", dated Jul. 1991.

Jancar et al., Measurement of the Elastic Modulus of Fibre–Reinforced composites Used as Orthbdonic Wires, vol. 5, *Journal of Materials Science: Materials in Medicine*, pp. 214–218 (1994).*

Goldberg et al., Screening of Matricles and Fibres for Reinforced Thermoplastics Intended for Dental Applications, vol. 28, *Journal of Biomedical Materials Research*, pp. 167–173 (1994)*

Jancar et al., Fibre–Reinforced themoplastic composites for Dentistry, vol. 4, *Journal of Materials Science: Materials in Medicine*, pp. 555–561 (Dec. 1993).*

* cited by examiner

*Primary Examiner*—Merrick Dixon

(57) ABSTRACT

Disclosed are profiles of fiber-reinforced polymeric plastic and a pultrusion apparatus and method for the manufacture thereof. The apparatus is preferably vertically disposed. As one or more fibers is fed into the apparatus, each fiber is spread and wetted with monomer resin in a bundle spreader, formed in a die, and then subjected in a curing chamber to a source of radiation which initates polymerization of the monomer, resulting in a fiber-reinforced polymeric plastic exiting from the pultrusion apparatus. Suitably, the radiation is ultraviolet, the monomer resin is methacrylate resin, and the fiber is quartz. The resultant profile is long and thin like a structural steel wire, but typically will have only ¼ the weight thereof while having a strength comparable thereto. Thus, the profile is useful as an orthodontic wire as a replacement instead of structural steel wires used as orthodontic wires. Several profiles can also be aggregated and the aggregate used to make, for instance, artificial limbs or other structural products.

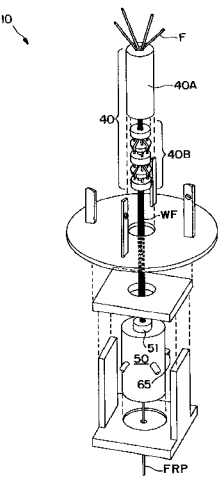

REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1–15 are cancelled.

\* \* \* \* \*